United States Patent
Wiemer et al.

(10) Patent No.: US 10,814,006 B2
(45) Date of Patent: Oct. 27, 2020

(54) FLUORESCENT PRODRUGS

(71) Applicants: UNIVERSITY OF IOWA RESEARCH FOUNDATION, Iowa City, IA (US); David F. Wiemer, Iowa City, IA (US); Rocky J. Barney, Iowa City, IA (US); Andrew Wiemer, Storrs, CT (US)

(72) Inventors: David F. Wiemer, Iowa City, IA (US); Rocky J. Barney, Iowa City, IA (US); Andrew Wiemer, Storrs, CT (US)

(73) Assignees: University of Iowa Research Foundation, Iowa City, IA (US); University of Connecticut, Farmington, CT (US)

( * ) Notice: Subject to any disclaimer, the term of this patent is extended or adjusted under 35 U.S.C. 154(b) by 0 days.

(21) Appl. No.: 15/745,321

(22) PCT Filed: Jul. 14, 2016

(86) PCT No.: PCT/US2016/042331
§ 371 (c)(1),
(2) Date: Jan. 16, 2018

(87) PCT Pub. No.: WO2017/011686
PCT Pub. Date: Jan. 19, 2017

(65) Prior Publication Data
US 2018/0207284 A1 Jul. 26, 2018

Related U.S. Application Data

(60) Provisional application No. 62/192,481, filed on Jul. 14, 2015.

(51) Int. Cl.
| *A61K 47/54* | (2017.01) |
| *G01N 33/50* | (2006.01) |
| *A61K 41/00* | (2020.01) |
| *A61K 31/683* | (2006.01) |
| *G01N 33/58* | (2006.01) |

(52) U.S. Cl.
CPC .......... *A61K 47/545* (2017.08); *A61K 31/683* (2013.01); *A61K 41/0038* (2013.01); *A61K 47/548* (2017.08); *G01N 33/5005* (2013.01); *G01N 33/5011* (2013.01); *G01N 33/582* (2013.01); *G01N 2800/7028* (2013.01)

(58) Field of Classification Search
None
See application file for complete search history.

(56) References Cited

U.S. PATENT DOCUMENTS

| 4,559,157 A | 12/1985 | Smith et al. |
| 4,608,392 A | 8/1986 | Jacquet et al. |
| 4,774,262 A | 9/1988 | Blanquet et al. |
| 4,820,508 A | 4/1989 | Wortzman |
| 4,938,949 A | 7/1990 | Borch et al. |
| 4,992,478 A | 2/1991 | Geria |
| 5,583,122 A | 12/1996 | Benedict et al. |
| 6,172,208 B1 | 1/2001 | Cook et al. |
| 6,727,234 B2 | 4/2004 | Wiemer et al. |
| 7,268,124 B2 | 9/2007 | Wiemer et al. |
| 8,664,181 B2 | 3/2014 | Kratz et al. |
| 2003/0162184 A1 | 8/2003 | Chou et al. |
| 2004/0167102 A1 | 8/2004 | Wiemer et al. |
| 2005/0208140 A1 | 9/2005 | Hilfinger et al. |
| 2007/0172832 A1* | 7/2007 | Lukhtanov ............ C07F 9/1411 435/6.11 |
| 2011/0112054 A1 | 5/2011 | Jomaa et al. |
| 2013/0018018 A1 | 1/2013 | Dong et al. |
| 2013/0225532 A1* | 8/2013 | Wong .................... C07F 9/6552 514/99 |

OTHER PUBLICATIONS

Kumar, S., et al., "PEG-Labeled Nucleotides and Nanopore Detection for Single Molecule DNA Sequencing by Synthesis" Scientific Reports, pp. 1-8 (Year: 2012).*
Renders, M., et al., "Enzymatic Polymerization of Phosphonate Nucleosides", Chembiochem, pp. 2883-2888 (Year: 2008).*
Xing, et al., "Lovastatin is antiarrhythmic in ischemic heart tissue by blocking triggered activity", J. of Invest. Med. 53(2), S368 (2005).
Yokoyama, et al., "Purification of a mammalian protein geranylgeranyltransferase. Formation and catalytic properties of an enzyme-geranylgeranyl pyrophosphate complex", J Biol Chem. 268(6), 4055-4060 (1993).
Zenitani, et al., "Gerfelin, a novel inhibitor of geranylgeranyl diphosphate synthase from Beauveria felina QN22047. I. Taxonomy, fermentation, isolation, and biological activities", J Antibiot (Tokyo). 56(7), 617-621 (2003).
Armstrong, et al., "cDNA cloning and expression of the alpha and beta subunits of rat Rab geranylgeranyl transferase.", J. Biol. Chem. 268, 12221-12229 (1993).
Benford, et al., "Farnesol and geranylgeraniol prevent activation of caspases by aminobisphosphonates: biochemical evidence for two distinct pharmacological classes of bisphosphonate drugs", Mol Pharmacol. 56(1), 131-140 (1999).

(Continued)

*Primary Examiner* — Michael G. Hartley
*Assistant Examiner* — Lance W Rider
(74) *Attorney, Agent, or Firm* — Viksins Harris Padys Malen LLP

(57) ABSTRACT

The invention provides a drug conjugate comprising: 1) a therapeutic agent that comprises a phosphate, phosphonate, carboxy, or phosphoramidate group, and 2) a fluorescent group linked to the phosphate, phosphonate, carboxy, or phosphoramidate group to form the corresponding ester and salts thereof. The conjugates are useful for therapy and as probes. The invention also provides therapeutic methods for treating diseases with conjugates of the invention as well as methods for determining optimal dosages of a conjugate or a therapeutic agent for a given patient using a conjugate of the invention.

2 Claims, 7 Drawing Sheets

(56) References Cited

OTHER PUBLICATIONS

Bergstrom, et al., "Alendronate is a specific, nanomolar inhibitor of farnesyl diphosphate synthase", Arch Biochem Biophys. 373(1), 231-241 (2000).
Cao, et al., "Photo-triggered Fluorescent Theranostic Prodrug for DNA Alkylating Agent Mechlorethamine Releasing and Spatiotemporal Monitoring", Organic & Biomolecular Chemistry (2015).
Cohen, et al., "Inhibition of human smooth muscle cell proliferation in culture by farnesyl pyrophosphate analogues, inhibitors of in vitro protein: Farnesyl transferase", Biochemical Pharmacology, vol. 57, No. 4, 365-474, 1999.
Ebetino, et al., "Recent Work on the Synthesis of Phosphonate-containing, Bone-active Heterocycles", Heterocycles 30, 855-862 (1990).
Ericsson, et al., "Distribution of prenyltransferases in rat tissues", J. Biol. Chem. 268, 832-838 (1993).
Ericsson, et al., "Human geranylgeranyl diphosphate synthase: isolation of the cDNA, chromosomal mapping and tissue expression", J. Lipid Res. 39(9), 1731-1739 (1998).
Fairlamb, et al., "Cycloisomerisation of modified terpenoid 1,6-enynes-synthesis of conformationally-restricted cyclic farnesyl analogues", Tetrahedron Letters, vol. 43, No. 30, 5327-5331, 2002.
Fisher, et al., "Alendronate mechanism of action: geranylgeraniol, an intermediate in the mevalonate pathway, prevents inhibition of osteoclast formation, bone resorption, and kinase activation in vitro", PNAS, 96(1), 133-138 (1999).
Foust, et al., "Mixed Aryl Phosphonate Prodrugs of a Butyrophilin Ligand", ACS Med. Chem. Lett. DOI: 10.1021/acsmedchemlett.7b00245, 5 pages (2017).
Fuse, et al., "Regulation of geranylgeranyl pyrophosphate synthase in the proliferation of rat FRTL-5 cells: involvement of both cAMP-PKA and PI3-AKT pathways", Biochem Biophys Res Commun. 315(4), 1147-1153 (2004).
Gerdes, et al., "Experimental determination and system level analysis of essential genes in *Escherichia coli* MG1655", J Bacteril 185 (19), 5673-5684 (2003).
Harly, et al., "Molecules and mechanisms implicated in the peculiar antigenic activation process of human Vγ9Vδ2 T cells", Frontiers in Immunology 5, 657, 13 pages (2014).
Holstein, et al., "Consequences of Mevalonate Depletion", J. Biol. Chem. 277, 10678-10682 (2002).
Holstein, et al., "Isoprenoid pyrophosphate analogues regulate expression of Ras-related proteins", Biochemistry 42(15), 4384-4391 (2003).
Holstein, et al., "Isoprenoids influence expression of Ras and Ras-related proteins", Biochemistry 41, 13698-13704 (2002).
Holstein, et al., "Phosphonate and bisphosphonate analogues of farnesyl pyrophosphate as potential inhibitors of farnesyl protein transferase", Bioorg Med Chem. 6(6), 6876-6894 (1998).
Hsiao, et al., "Synthesis of a Phosphoantigen Prodrug that Potently Activates V9V2 T-Lymphocytes", Chemistry & Biology, vol. 21, 945-954 (2014).
Hutchinson, et al., "Synthesis of alkylated methylene bisphosphonates via organothallium intermediates", Journal of Organometallic Chemistry, vol. 291, No. 2, 145-151, 1985.
Karunakaran, et al., "The Vγ9Vδ2 T Cell Antigen Receptor and Butyrophilin-3 A1: Models of Interaction, the Possibility of Co-Evolution, and the Case of Dendritic Epidermal T Cells", Frontiers in Immunology 5, 648, 13 pages (2014).
Keller, et al., "Mechanism of aminobisphosphonate action: characterization of alendronate inhibition of the isoprenoid pathway", Biochem Biophys Res Commun. 266, 560-563 (1999).
Kornberg, et al., "Measurement of Transmembrane Potentials in Phospholipid Vesicles", PNAS 69(6), 1508-1513 (1972).
Lee, et al., "Perspectives on the development of acyclic nucleotide analogs as antiviral drugs", Antiviral Research 71, 254-259 (2006).
Luckman, et al., "Nitrogen-containing bisphosphonates inhibit the mevalonate pathway and prevent post-translational prenylation of GTP-binding proteins, including Ras", J. Bone Miner. Res. 13(4), 581-589 (1998).
Maffre-Lafon, et al., "Solid Phase Synthesis of Phosphonopeptides from Fmoc Phosphonopeptides", Tetrahedron Letters, vol. 35, No. 24, 4097-4098 (1994).
Martin, et al., "Bisphosphonates inhibit the growth of Trypanosoma brucei, Trypanosoma cruzi, Leishmania donovani, Toxoplasma gondii, and Plasmodium falciparum: a potential route to chemotherapy", J. Med. Chem. 44(6), 909-916 (2001).
McKenna, et al., "The facile dealkylation of phosphonic acid dialkyl esters by bromotrimethylsilane", Tetrahedron Lett. 18, 155-158 (1977).
Moomaw, et al., "Mammalian protein geranylgeranyltransferase. Subunit composition and metal requirements", J. Biol. Chem. 267, 17438-17443 (1992).
Morita, et al., "Nonpeptide antigens, presentation mechanisms, and immunological memory of human Vγ2Vδ2 T cells: discriminating friend from foe through the recognition of prenyl pyrophosphate antigens", Immunological Reviews 215, 59-76 (2007).
Muhlbauer, et al., "Effect of various polyphosphonates on ectopic calcification and bone resorption in rats", Mineral and Electrolyte Metabolism, vol. 5, No. 6, 296-303, 1981.
Patent Cooperation Treaty, International Searching Authority, Search Report and Written Opinion for PCT/US2016/042331, 11 pages (dated Sep. 30, 2016).
Pertusati, et al., "Medicinal chemistry of nucleoside phosphonate prodrugs for antiviral therapy", Antivir Chem Chemother 22(5), 181-203 (2012).
Quimby, et al., "Metalated methylenediphosphate esters. Preparation, characterisation and synthetic applications", Journal of Organometallic Chemistry, vol. 291, No. 2, 145-151, (1968).
Reiss, et al., "Inhibition of purified p21ras farnesyl:protein transferase by Cys-AAX tetrapeptides", Cell 62(1), 81-88 (1990).
Reszka, et al., "Bisphosphonates Act Directly on the Osteoclast to Induce Caspase Cleavage of Mst1 Kinase during Apoptosis", J. Biol. Chem. 274, 34967-34973 (1999).
Sagami, et al., "Studies on geranylgeranyl diphosphate synthase from rat liver: specific inhibition by 3-azageranylgeranyl diphosphate", Arch Biochem Biophys. 297(2), 314-320 (1992).
Shull, et al., "Synthesis and biological activity of isoprenoid bisphosphonates", Bioorg Med Chem., 14(12), 4130-4136 (2006).
Spear, et al., "Molecular cloning and promoter analysis of the rat liver farnesyl diphosphate synthase gene", J. Biol. Chem. 267, 14462-14469 (1992).
Szabo, et al., "Inhibition of geranylgeranyl diphosphate synthase by bisphosphonates and diphosphates: a potential route to new bone antiresorption and antiparasitic agents", J Med Chem. 45(11), 2185-2196 (2002).
Valentinjn, et al., "Synthesis of Pyrophosphonic Acid Analogues of Farnesyl Pyrophosphate", Tetrahedron, vol. 51, No. 7, 2099-2108, (1995).
Van Beek, et al., "Farnesyl pyrophosphate synthase is the molecular target of nitrogen-containing bisphosphonates", Biochem Biophys Res Commun. 264(1), 108-111 (1999).
Van Beek, et al., "The role of geranylgeranylation in bone resorption and its suppression by bisphosphonates in fetal bone explants in vitro: A clue to the mechanism of action of nitrogen-containing bisphosphonates", J Bone Miner Res. 14(5), 722-729 (1999).
Vepsalainen, et al., "Bisphosphonate prodrugs: a new synthetic strategy to tetraacyloxymethyl esters of methylenebisphosphonates", Tetrahedron. Lett. 40, 8491-8493 (1999).
Vicent, et al., "The Branch Point Enzyme of the Mevalonate Pathway for Protein Prenylation Is Overexpressed in the bb/ob Mouse and Induced by Adipogenesis", Mol. Cellular Biol. 20, 2158-2166 (2000).
Virtanen, et al., "Alendronate inhibits invasion of PC-3 prostate cancer cells by affecting the mevalonate pathway", Cancer Res. 62(9), 2708-2714 (2002).
Westheimer, et al., "Why nature chose phosphates", Science 235 (4793), 1173-1178 (1987).

(56) References Cited

OTHER PUBLICATIONS

Wiemer, et al., "Isoprenoid metabolism as a therapeutic target in gram-negative pathogens", Current Topics in Medicinal Chemistry 10(18), 1858-1871 (2010).

Wiemer, et al., "Opportunities and challenges in development of phosphoantigens as Vγ9Vδ2 T cell agonists", Biochem Pharmacol 89(3), 301-312 (2014).

Wiemer, et al., "Prodrugs of Phosphonates and Phosphates: Crossing the Membrane Barrier", Top Curr Chem DOI: 10.1007/128_2014_561, 46 pages (2014).

* cited by examiner

FLUORESCENT PRODRUGS

RELATED APPLICATION

This application claims priority to U.S. Provisional Patent Application No. 62/192,481 filed Jul. 14, 2015, the entirety of which is incorporated herein by reference.

STATEMENT REGARDING FEDERALLY SPONSORED RESEARCH

This invention was made with government support under CA186935 awarded by the National Institutes of Health. The government has certain rights in the invention.

BACKGROUND OF THE INVENTION

A variety of drugs and other biologically interesting molecules contain phosphate or phosphonate substructures (Westheimer, F. H., *Science*, 1987, 235, 4793, 1173-1178). However, the negative charge of such compounds at physiological pH frequently acts as a barrier to rapid cellular entry (Kornberg, R. D., et al., *Proceedings of the National Academy of Sciences of the United States of America*, 1972, 69, 6, 1508-1513). As such, development of cell-cleavable protecting groups that increase in vivo absorption is of great interest with several phosphonate "prodrugs" recently achieving clinical status (Wiemer, A. J. and D. F. Wiemer, *Top Curr Chem*, 2015, 360, 115-60). While cell-cleavable phosphoester (Lee, W. A. and J. C. Martin, *Antiviral Research*, 2006, 71, 254-259) and phosphoamidate (Pertusati, F., et al., *Antivir Chem Chemother*, 2012, 22, 5, 181-203) protecting groups effectively increase cellular uptake, it remains challenging to use these compounds to assess biological mechanisms in real-time because concentrations of compounds in live cells cannot be readily assessed.

(E)-4-Hydroxy-3-methyl-but-2-enyl diphosphate (HMBPP) is an intermediate of isoprenoid metabolism found in bacteria and other microorganisms (Wiemer, A. J., C.-H. C. Hsiao, and D. F. Wiemer, *Current Topics in Medicinal Chemistry*, 2010, 10, 18, 1858-1871). HMBPP synthesis is required for bacteria growth (Gerdes, S. Y., et al., *J Bacteriol*, 2003, 185, 19, 5673-84) and it also functions as a potent pathogen-associated molecular pattern (PAMP) that stimulates an immune response from human gamma delta T cells (Morita, C. T., et al., *Immunological Reviews*, 2007, 215, 59-76). However, the mechanisms of HMBPP immunostimulation are currently a topic of intense debate (Karunakaran, M. M. and T. Hellmann, *Frontiers in Immunology*, 2014, 5; and Harly, C., C.-M. Peigné, and E. Scotet, *Frontiers in Immunology*, 2014, 5). Therefore, development of HMBPP analogs which can contribute to understanding its immunostimulatory mechanism are desired (Wiemer, D. F. and A. J. Wiemer, *Biochem Pharmacol*, 2014, 89, 3, 301-12).

Currently there is a need for agents that are useful for treating or preventing diseases (e.g. cancer) and for cancer immunotherapy agents. There is also a need for detectable probes that can be used to study the pharmacology of diseases and therapeutic agents.

SUMMARY OF THE INVENTION

Enzymatically-cleavable protecting groups are often required for efficient cellular delivery of drugs or chemical probes that contain carboxylates, phosphonates, and phosphates. Although several protecting groups have achieved clinical success, it remains difficult in live cells to use prodrugs to clarify biological mechanisms in space and time with precise clarity. The invention provides a protecting strategy that uses fluorescent ester derivatives (e.g. 7-methoxycoumarin-3-carboxylic acid (MOCCA or CCOM) ester derivatives) as carboxylate, phosphonate, and phosphate protecting groups. The fluorescent protecting groups deliver the resulting conjugates intracellularly, with high efficiency and low toxicity. The free fluorescent protecting group, but not the corresponding esters, typically exhibit strong pH sensitivity, allowing for no-wash kinetic analysis of is biological deprotection by conventional fluorescence plate readers. Modified phosphoantigens have been found to display similar biological activity to pivaloyloxymethyl (POM)-modified phosphoantigens and reveal that phosphoantigen esters are internalized into cells within hours of administration. The conjugates of the invention include fluorescent protecting groups that are both functional drug delivery tools and useful biological probes for monitoring the exquisite rates of cellular uptake of the conjugates.

Accordingly the invention provides a conjugate comprising: 1) a therapeutic agent that comprises a phosphate, phosphonate, carboxy, or phosphoramidate group, and 2) a fluorescent group linked to the phosphate, phosphonate, carboxy, or phosphoramidate group to form the corresponding ester, or a salt thereof.

The invention also provides a pharmaceutical composition comprising a conjugate of the invention, or a pharmaceutically acceptable salt thereof, and a pharmaceutically acceptable carrier.

The invention also provides a conjugate of the invention, or a pharmaceutically acceptable salt thereof, for use in medical therapy.

The invention also provides a conjugate of the invention, or a pharmaceutically acceptable salt thereof, for the prophylactic or therapeutic treatment of cancer.

The invention also provides the use of a conjugate of the invention, or a pharmaceutically acceptable salt thereof, to prepare a medicament for treating cancer in an animal (e.g. a mammal such as a human).

The invention also provides synthetic processes and intermediates disclosed herein that are useful for preparing a conjugate of the invention.

The invention also provides a conjugate of the invention (e.g. a conjugate comprising a therapeutic agent that has anti-infective activity or immune modulating activity), or a pharmaceutically acceptable salt thereof, for the prophylactic or therapeutic treatment of infections and/or immune disorders.

The invention also provides the use of a conjugate of the invention (e.g. a conjugate comprising a therapeutic agent that has anti-infective activity or immune nodulating activity), or a pharmaceutically acceptable salt thereof, to prepare a medicament for treating infections and/or immune disorders in an animal (e.g. a mammal such as a human).

Phosphoantigen-sensitive Vγ9Vδ2 T cells are important responders to infections and malignancy. However, the mechanisms by which phosphoantigens stimulate Vγ9Vδ2 T cells are unclear. Phosphoantigen prodrugs were prepared and used to demonstrate that intracellular delivery of phosphoantigens is required for their activity. The pivaloyloxymethyl prodrug provides stronger stimulation of Vγ9Vδ2 T cells from human peripheral blood and greater ability to induce lysis of Daudi lymphoma cells relative to the previously most potent compound, (E)-4-hydroxy-3-methyl-but-2-enyl pyrophosphate (HMBPP). Using molecular approaches, nuclear magnetic resonance (NMR) spectroscopy and isothermal titration calorimetry (ITC) a high binding affinity between phosphoantigens and the intracellular region of butyrophilin 3A1 (BTN3A1) has been shown, localized to the PRY/SPRY (B30.2) domain but also affecting the membrane proximal region. Collectively, these findings not only promote a novel compound/approach for cancer immunotherapy, but also unravel fundamental aspects of the molecular mechanisms of Vγ9Vδ2 T cell activation by phosphoantigens.

DETAILED DESCRIPTION

Figure 1:
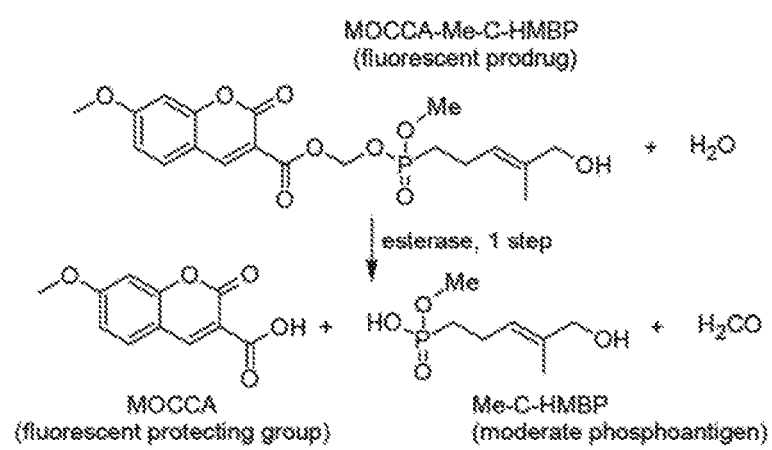
FIG. 1. A) Expected cellular metabolism of MOCCA-Me-C-HMBP. B) Expected cellular metabolism of MOCCA-POM-C-HMBP.
Figure 1:
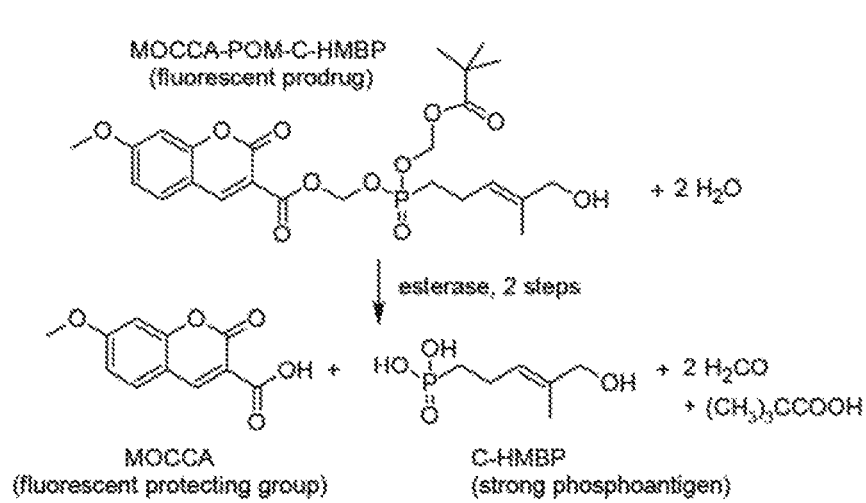

It will be appreciated by those skilled in the art that conjugates having a chiral center may exist in and be isolated in optically active and racemic forms. Some conjugates may exhibit polymorphism. It is to be understood that the present invention encompasses any racemic, optically-active, polymorphic, or stereoisomeric form, or mixtures thereof, of a conjugate of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a compound of formula I through the carboxy terminus, the amino terminus, or through any other convenient point of attachment, such as, for example, through the sulfur of cysteine.

The conjugates of the invention comprise a therapeutic agent that is linked to a fluorescent group through a linkage that is readily degradable once the compound is within the cell. As used herein, "linked" includes a direct covalent bond as well as covalent attachment through a linking group. Suitable linking groups include a ($C_1$-$C_6$) alkylene (e.g. methylene), an acyloxy ester of a phosphonic or carboxylic acid ester, or a phosphonamidate derivative of a phosphonic acid where either the amide or the ester (or both) include a fluorescent moiety, attached by a variable linker. Suitable fluorescent groups including fluorescein, coumarin, FITC, and CFSE, and derivatives thereof.

The term "therapeutic agent" includes compounds that have a therapeutic or biological effect on an animal (e.g. a mammal). In one embodiment, the therapeutic agent excludes nucleic acids (e.g. DNA and RNA). In one embodiment, the therapeutic agent excludes proteins (e.g. proteins having five or more amino acids in sequence). In one embodiment, the therapeutic agent excludes nucleic acids (e.g. DNA and RNA) and proteins (e.g. proteins having five or more amino acids in sequence). In one embodiment the therapeutic agent is a small organic molecule (e.g. a small molecule having a molecular weight of less than about 800 u). In one embodiment the therapeutic agent is a small organic molecule having a molecular weight of less than about 600 u. In one embodiment the therapeutic agent is a small organic molecule having a molecular weight of less than about 500 u. In one embodiment the therapeutic agent is a small organic molecule having a molecular weight of at least about 200 u and less than about 800 u. In one embodiment the therapeutic agent is a small organic molecule having a molecular weight of at least about 200 u and less than about 600 u. In one embodiment the therapeutic agent is a small molecule that has anti-cancer (e.g. anti-leukemia) properties. In one embodiment the therapeutic agent is a small molecule that has anti-infective properties. In one embodiment the therapeutic agent is a small molecule that has immune-modulating properties.

In one embodiment the invention provides a method comprising: obtaining a biological sample from a mammal comprising one or more cells; contacting a conjugate of the invention with the biological sample under conditions whereby the conjugate enters the cells; and measuring the conjugate's fluorescent intensity within the cells or the decrease in fluorescence intensity outside the cells. In one embodiment, such a method can be used to determine an appropriate dose of the conjugate or the therapeutic agent comprised therein to administer to the mammal. For example, in order to determine the appropriate dosage of a therapeutic agent that has anti-leukemia properties the invention provides a method comprising obtaining white cells from a mammal by drawing blood from the mammal, contacting the white cells with a conjugate of the invention that comprises a therapeutic agent having anti-leukemia properties to establish the rate/amount of uptake, and using the rate or uptake to design a specific dosage (e.g. of the conjugate or of the therapeutic agent) for that mammal.

When a bond in a conjugate formula herein is drawn in a non-stereochemical manner (e.g. flat), the atom to which the bond is attached includes all stereochemical possibilities. When a bond in a conjugate formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the conjugate may be at least 51% the absolute stereoisomer depicted. In another embodiment, the conjugate may be at least 60% the absolute stereoisomer depicted. In another embodiment, the conjugate may be at least 80% the absolute stereoisomer depicted. In another embodiment, the conjugate may be at least 90% the absolute stereoisomer depicted. In another embodiment, the conjugate may be at least 95 the absolute stereoisomer depicted. In another embodiment, the conjugate may be at least 99% the absolute stereoisomer depicted.

A prodrug is a compound that can be converted under physiological conditions to a therapeutic or otherwise biologically active agent. The term "prodrug moiety" includes cleavable groups that can be appended to a therapeutic agent to form a prodrug. For example, the term prodrug moiety includes groups that form cleavable esters, cleavable anhydrides, and cleavable amides, such as amino acid residues and polypeptide chains of two or more (e.g., two, three or four) amino acid residues that can be linked to a therapeutic agent to form a prodrug. Phosphonate and phosphate prodrug moieties are known to include acyloxy esters and phenyl (or substituted phenyl) phosphoramidates (Wiemer, A. J. and D. F. Wiemer, *Top Curr Chem*, 2015, 360, 115-60). In one embodiment, the term prodrug moiety is a "cell cleavable group," which can be cleaved under physiological conditions inside a cell to provide a therapeutic agent, for example the pivaloyloxymethyl ester POM group. For additional examples of prodrug derivatives, see a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 "Design and Application of Prodrugs," by H. Bundgaard p. 113-191 (1991); c) H. Bundgaard, *Advanced Drug Delivery Reviews*, 8:1-38 (1992); d) H. Bundgaard, et al., *Journal of Pharmaceutical Sciences*, 77:285 (1988); and e) N. Kakeya, et al., *Chem. Pharm. Bull.*, 32:692 (1984).

Processes and synthetic intermediates that are useful for preparing conjugates of the invention are provided as further embodiments of the invention and are illustrated by the Schemes and Examples herein. In preparing conjugates of the invention, protection of certain functional groups may be beneficial. The desirability of such protection will vary depending on the nature of the functionality and the conditions of the preparation methods. For example, when preparing a conjugate comprising a therapeutic agent of formula:

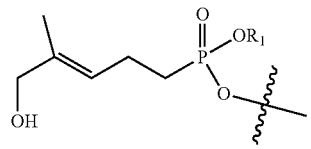

wherein $R^1$ is H, it may be beneficial to prepare a corresponding protected compound wherein $R^1$ is a protecting group or prodrug moiety. Compounds comprising one or more protecting groups are useful as synthetic intermediates for preparing other conjugates of the invention. Compounds comprising one or more protecting groups may also possess useful biological activities. Accordingly, in one embodiment the invention provides compounds and conjugates that comprise one or more protecting groups. Suitable protecting groups, as well as suitable conditions for their incorporation and removal are known, see T. W. Greene, et al. *Greene's Protective Groups in Organic Synthesis*. New York: Wiley Interscience, 2006.

In cases where a conjugate is sufficiently basic or acidic, a salt of a conjugate can be useful as an intermediate for isolating or purifying another conjugate. Additionally, administration of a conjugate as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic conjugate such as an amine with a suitable acid affording a physiologically acceptable anion. Alkali metal (for example, sodium, potassium or lithium) or alkaline earth metal (for example calcium) salts of carboxylic acids can also be made.

The conjugates can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the conjugates may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the conjugate may be combined with one or more excipients and used in the form of ingestible tablets, buccal tablets, troches, capsules, elixirs, suspensions, syrups, wafers, and the like. Such compositions and preparations should contain at least 0.1% of active conjugate. The percentage of the compositions and preparations may, of course, be varied and may conveniently be between about 2 to about 60% of the weight of a given unit dosage form. The amount of conjugate in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the conjugate, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the conjugate may be incorporated into sustained-release preparations and devices.

The conjugate may also be administered intravenously or intraperitoneally by infusion or injection. Solutions of the active conjugate can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the conjugate in the required amount in the appropriate solvent with various types of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the conjugates may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present conjugates can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the conjugates to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the conjugates can be determined by comparing their in vitro activity, and in vivo activity in animal models. Methods for the extrapolation of effective dosages in mice, and other animals, to humans are known to the art; for example, see U.S. Pat. No. 4,938,949.

The amount of the conjugate, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

EXAMPLES

Example 1. Synthesis of a Representative Conjugate of the Invention (Mono MOCCA Mono Methyl Phosphonate)

A representative conjugate of the invention was prepared as illustrated and described below.

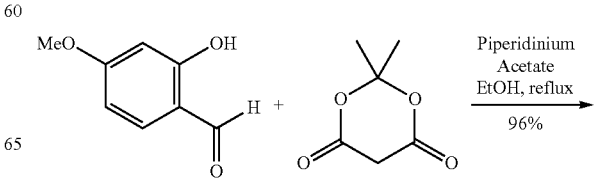

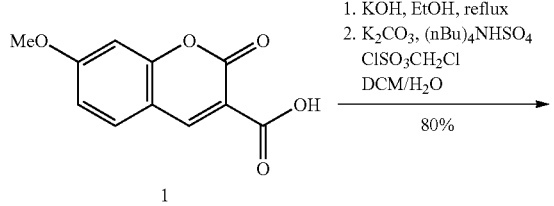

a. Preparation of 7-Methoxy-2-oxo-2H-chromene-3-carboxylic acid

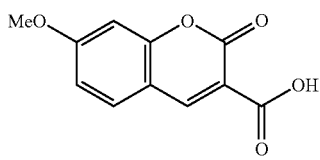 [SMILES: COc1ccc2cc(C(=O)O)c(=O)oc2c1]

2-Hydroxy-4-methoxybenzaldehyde (2.99 g, 19.7 mmol), Meldrum's acid (2.88 g, 19.8 mmol), and piperidinium acetate (64 mg, 0.44 mmol) were dissolved in ethanol, the solution was heated at reflux for 3 hours, and then it was cooled to 0° C. in an ice bath resulting in a precipitate. The precipitate was isolated by filtration and recrystallized from hot ethanol. The product was isolated by filtration to give a slightly yellow solid in 96% yield (4.17 g), with $^1$H NMR data consistent with literature data (Caron, K., et al., *Org. Biomol. Chem.* 2011, 9, 185-197).

b. Preparation of 7-Methoxy-2-oxo-2H-chromene-3-carboxylic acid chloromethyl ester 2

The carboxylic acid 1 (1.10 g, 5.02 mmol) and KOH (0.28 g, 5.02 mmol) were dissolved in ethanol and the solution was heated at reflux for 4 hours.² After the solution was concentrated in vacuo, the resulting solid was dissolved in water (20 mL) and dichloromethane (20 mL) and the solution was cooled to 0° C. Potassium carbonate (6.93 g, 50.0 mmol), tetrabutylammonium hydrogen sulfate (0.41 g, 1.21 mmol), and chloromethyl chlorosulfate (1.52 mL, 15.1 mmol) were added. The solution was stirred vigorously for 10 mins and then allowed to stir for 48 hr. The organic portion was separated and the aqueous layer was extracted with dichloromethane. The organic portions were combined and washed with brine, dried (NaSO$_4$), and filtered, and the filtrate was concentrated in vacuo. The residue was purified by column chromatography (8% EtOH in dichloromethane) to give the desired product 2 (1.1 g, 80%): $^1$H NMR (400 MHz, CDCl$_3$) δ 8.62 (s, 1H), 7.55 (d, J=8.8 Hz, 1H), 6.93 (dd, J=8.8, 2.4 Hz, 1H), 6.83 (d, J=2.4 Hz, 1H), 5.95 (s, 2H), 3.93 (s, 3H); $^{13}$C NMR (75 MHz, DMSO) δ 165.4, 160.6, 157.3, 155.7, 151.0, 132.0, 113.4, 111.2, 111.0, 100.2, 69.8, 56.2; HRMS (ES) calcd for C$_{12}$H$_9$O$_5$ClNa [M$^+$+Na] 291.0036; found: 291.0038. See Ingram, A. M., et al., *Org. Biomol. Chem* 2006, 4, 2869-2873 for related synthetic processes.

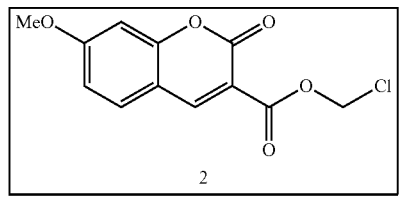

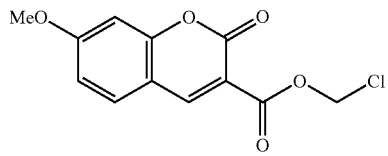

c. Preparation of Ammonium Salt 4

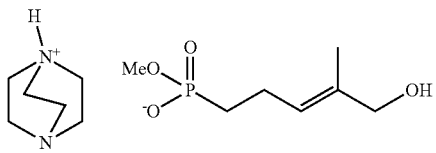

4

(5-Hydroxy-4-methyl-pent-3-enyl)-phosphonic acid dimethyl ester (Hsiao, C.-H., et al., *Chem. Biol.* (*Oxford, U. K.*) 2014, 21, 945-954; 0.18 g, 0.87 mmol) and 1,4-diazabicyclo [2.2.2] octane (0.09 g, 0.87 mmol) were dissolved in acetonitrile and the reaction mixture was heated at reflux overnight. The solution was concentrated in vacuo and used without further purification, giving the desired product 4 as a brown residue in 61% yield (0.17 g): $^1$H NMR (400 MHz, D$_2$O) δ 5.38-5.44 (m, 1H), 3.89 (s, 2H), 3.46 (d, J$_{PH}$=10.5 Hz, 3H), 3.30-3.33 (m, 6H), 3.10-3.15 (m, 6H), 2.15-2.19 (m, 2H), 1.53-1.61 (m, 5H); $^{13}$C NMR (125 MHz, D$_2$O) δ 135.3, 127.1 (d, J$_{PC}$=16.6 Hz), 68.1, 54.6, 54.6, 54.6, 52.2, 52.2, 52.1, 51.6 (d, J$_{PC}$=5.4 Hz), 25.8 (d, J$_{PC}$=134.0 Hz), 21.8 (d, J$_{PC}$=4.8 Hz), 12.9; $^{31}$P NMR (161 MHz, CDCl$_3$)+ 29.3; HRMS (ES$^-$) calcd for C$_7$H$_{14}$O$_4$P [M$^-$-DABCO] 193.0641; found: 193.0630.

d. Preparation of Phosphonate 5

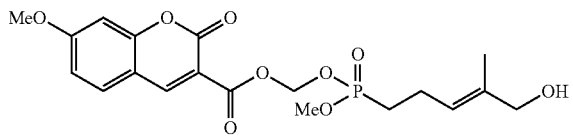

5

The phosphonate salt 4 (170 mg, 0.53 mmol), sodium iodide (0.12 g, 0.80 mmol), and chloromethyl ester 2 (0.21 g, 0.80 mmol) were dissolved in acetonitrile (5 mL) and the resulting solution was heated at reflux overnight. The reaction was then quenched by addition of brine and extracted with dichloromethane. The combined organic portions were washed with saturated Na$_2$S$_2$O$_3$, dried (NaSO$_4$), and filtered, and the filtrate was concentrated in vacuo. The residue was purified by column chromatography (5% EtOH in dichloromethane) to give the product 5 as a white solid (142 mg, 63%): $^1$H NMR (500 MHz, CDCl$_3$) δ 8.59 (s, 1H), 7.51 (d, J=8.6 Hz, 1H), 6.88 (dd, J=8.6 Hz, 2.2 Hz, 1H), 6.78 (d, J=2.2 Hz, 1H), 5.84 (d, J$_{PH}$=13.1 Hz, 2H), 5.37-5.39 (m, 1H), 3.93 (s, 2H), 3.89 (s, 3H), 3.74 (d, J$_{PH}$=10.9 Hz, 3H), 2.41 (br s, 1H), 2.28-2.35 (m, 2H), 1.86-1.93 (m, 2H), 1.60 (s, 3H); $^{13}$C NMR (125 MHz, CDCl$_3$) δ 165.8, 161.7, 157.8, 156.5, 150.4, 136.4 (d, J$_{PC}$=1.5 Hz), 131.1 (d, J$_{PC}$=15.9 Hz), 113.9, 112.0, 111.4, 100.3, 82.2 (d, J$_{PC}$=6.0 Hz) 67.9, 56.0, 52.0 (d, J$_{PC}$=7.1 Hz), 25.5 (d, J$_{PC}$=139.4 Hz), 20.3 (d, J$_{PC}$=4.9 Hz), 13.5; $^{31}$P NMR (202 MHz, CDCl$_3$)+33.8; HRMS (ES$^+$) calcd for C$_{19}$H$_{24}$O$_9$P [(M+H)$^+$] 427.1158; found 427.1164.

Example 2. Synthesis of a Representative Conjugate of the Invention (Mono MOCCA Mono POM Phosphonate)

A representative conjugate of the invention was prepared as illustrated and described below.

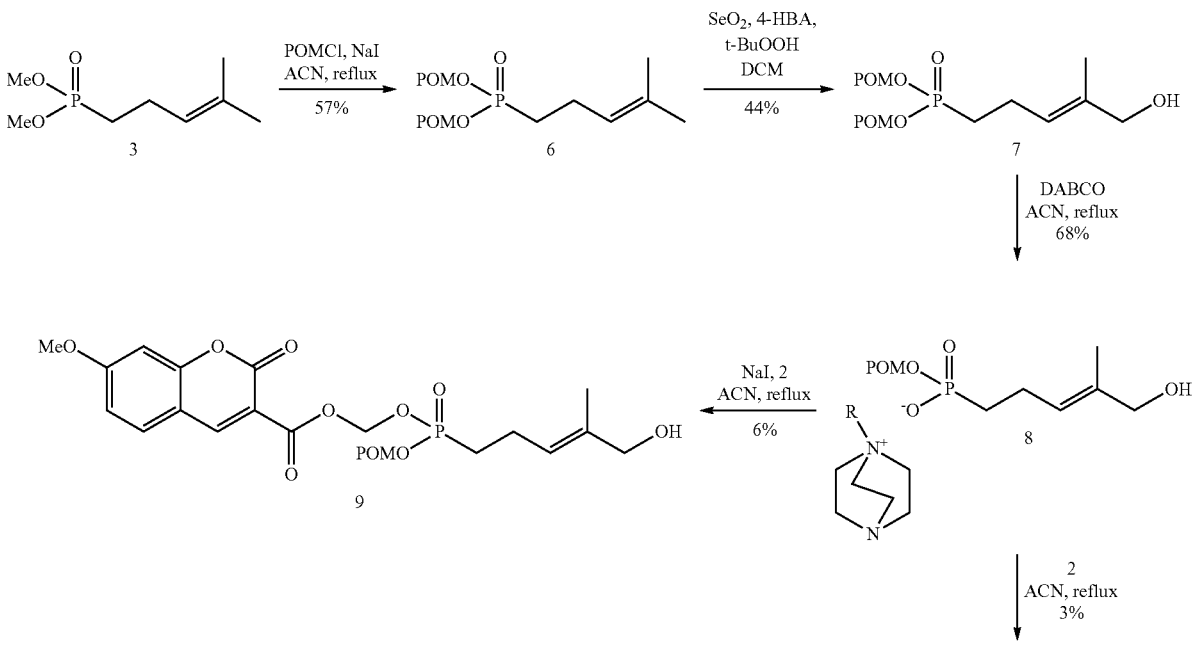

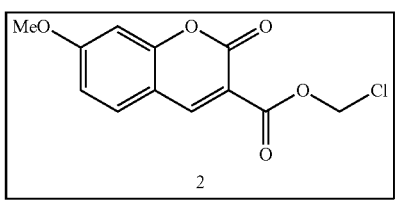

2

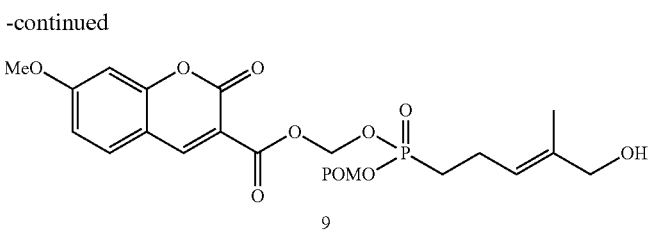

9 a. Preparation of Phosphonate Ester 6

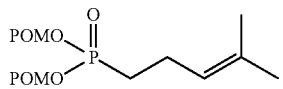

6

(4-Methyl-pent-3-enyl)-phosphonic acid dimethyl ester (3, 1.02 g, 5.29 mmol), sodium iodide (1.63 g, 10.9 mmol), and chloromethyl pivalate (2.43 mL, 16.7 mmol) were dissolved in acetonitrile (5 mL) and the solution was heated at reflux overnight. The reaction was quenched by addition of water and extracted with diethyl ether. The combined organic portions were washed with $Na_2S_2O_3$, dried ($NaSO_4$), and filtered, and the filtrate was concentrated in vacuo. The residue was purified by column chromatography (1:1 $Et_2O$/hexanes) to afford the product 6 as a clear oil (1.17 g, 57%). Both the $^1H$ and $^{31}P$ NMR data were consistent with literature data (Hsiao, C.-H., et al., Chem. Biol. (Oxford, U. K.) 2014, 21, 945-954).

b. Preparation of Phosphonate Ester 7

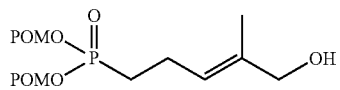

7

The phosphonate ester 6 (0.60 g, 1.52 mmol), selenium dioxide (0.08 g, 0.76 mmol), p-hydroxybenzonic acid (0.10 g, 0.76 mmol), and tert-butylhydroperoxide (0.74 mL, 4.56 mmol) were added to dichloromethane (10 mL). After the reaction mixture was cooled to 0° C. and allowed to stir overnight, it was quenched by addition of brine and extracted with dichloromethane. The combined organic portions were washed with saturated $Na_2S_2O_3$, dried ($Na_2SO_4$), and filtered, and the filtrate was concentrated in vacuo. The residue was purified by column chromatography (ether) and the product 7 was isolated as a yellow oil (270 mg, 44%). Both the $^1H$ and $^{31}P$ NMR data were consistent with literature data (Hsiao, C.-H., et al., Chem. Biol. (Oxford, U. K.) 2014, 21, 945-954).

c. Preparation of Phosphonate Salt 8

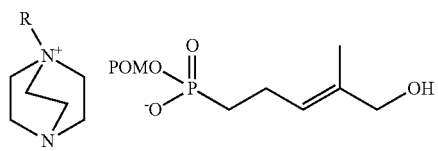

8

Ester 7 (0.47 g, 1.15 mmol) and 1,4-diazabicyclo[2.2.2]octane (0.13 g, 1.15 mmol) were dissolved in acetonitrile and the reaction mixture was heated at reflux overnight. The reaction was quenched by addition of ether and extracted with water. The aqueous portions were combined and concentrated in vacuo, giving the desired product 8 as a brown residue (390 mg, 68%) that was used in the following reaction without further purification.

d. Preparation of Mixed Ester 9

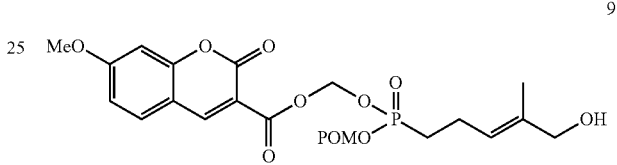

9

The salt 8 (0.20 g, 0.39 mmol), sodium iodide (0.09 g, 0.59 mmol), and 7-methoxy-2-oxo-2H-chromene-3-carboxychloromethyl ester (2, 0.16 g, 0.59 mmol) were dissolved in acetonitrile (5 mL). The resulting solution was heated at reflux overnight, and then quenched by addition of brine and extracted with dichloromethane. The organic portions were washed with saturated $Na_2S_2O_3$, dried ($NaSO_4$), and filtered, and the filtrate was concentrated in vacuo. The residue was purified by column chromatography (5% EtOH in dichloromethane) to afford the desired product 9 as a white solid (9 mg, 6%): $^1H$ NMR (400 MHz, $CDCl_3$) δ 8.64 (s, 1H), 7.56 (d, J=8.9 Hz, 1H), 6.92 (dd, J=8.9 Hz, 2.4 Hz, 1H), 6.83 (d, J=2.4 Hz, 1H), 5.87-5.90 (m, 2H), 5.66-5.76 (m, 2H), 5.39-5.44 (m, 1H), 4.43 (s, 2H), 3.93 (s, 3H), 2.31-2.41 (m, 2H), 1.91-2.01 (m, 2H), 1.65 (s, 3H), 1.58 (br s, 1H), 1.25 (s, 9H); $^{31}P$ NMR (161 MHz, $CDCl_3$) δ 32.4.

Example 3. Conjugate Evaluation

Reagents and Supplies

PE-conjugated anti-human CD3 was obtained from eBioscience (San Diego, Calif.). Human interleukin 2 was obtained from Miltenyi (San Diego, Calif.). Annexin-V FITC was obtained from BD Biosciences (San Jose, Calif.). HMBPP was obtained from Echelon Biosciences (Salt Lake City, Utah). CellQuantiBlue was obtained from BioAssay Systems (Hayward, Calif.). FITC-anti-human gamma delta TCR antibody (5A6.E91) and DiD cell stain was purchased from Thermo Fisher Scientific (Rockford, Ill.). Fetal bovine serum and all other tissue culture supplies also were obtained from Thermo Fisher. Polyester backed silica G plates, with UV 256 were obtained from Sorbtech technologies (Norcross, Ga.). Human PMBCs were isolated from blood from Research Blood Components (Brighton, Mass.). K562 cells were obtained from ATCC (Manassas, Va.).

Cell Culture

K562 cells were cultured in fresh K562 media (RPMI-1640, 10% heat-inactivated Fetalclone III, 1× penicillin/streptomycin). Daudi and RPMI-8226 cells were cultured in fresh Daudi/RPMI media (RPMI-1640, 10% heat-inactivated FBS, 1× penicillin/streptomycin). Gamma delta T cells were cultured as described previously [12]. Briefly, cells were expanded from peripheral blood mononuclear cells in fresh T cell media (RPMI-1640, 10% heat-inactivated FBS, 1× HEPES, pyruvate, non-essential amino acids, penicillin/streptomycin, beta-mercaptoethanol) and added to 6-well plates. Cells were stimulated with test compounds for three days at concentrations indicated in the text. Cells were washed twice then cultured for another eleven days after compound removal. Human interleukin 2 (5 ng/mL) was supplemented every three days. Experiments were performed at least three times independently using at least two different blood donors.

Thin Layer Chromatography

Compounds were exposed to cells, plasma, media, or PBS as indicated in the text in 100 μL volumes. Compounds were extracted from all biological mixtures using 200 μL of organic solvent containing 95% dichloromethane, 5% ethanol, and 0.25% glacial acetic acid. Extracts were separated by normal phase flash chromatography using 95% dichloromethane, 5% ethanol, and 0.25% glacial acetic acid as the mobile phase. Compounds were visualized under UV light.

Flow Cytometry

Total gamma delta TCR was labeled using FITC-anti-human Pan gamma delta TCR antibody and CD3 was labeled using PE-conjugated anti-human CD3 as described [12].

Killing Assay

The killing assay was performed as described with slight modification [12, 13]. T cells were expanded from PMBCs by stimulation with 0.01 μM HMBPP. Cells were purified by negative selection using a kit (Miltenyi). K562 cells were stained with DiD (2 minutes in 4 μM DiD in BSA/PBS), quenched by addition of an equal volume of FBS, and washed twice in T cell media. 6×10³ K562 cells were mixed with 3×10⁴ T cells and test compounds to a final volume of 100 μL. Mixtures were incubated for 4 hours at 37 degrees then placed on ice for 5 minutes. Annexin V FITC (3 μL) was added for 15 minutes on ice, then cells were diluted by addition of 200 μL binding buffer (BD) and immediately analyzed by flow cytometry.

Proliferation Assay

To assess K562 proliferation, 10000 cells/well were added to 96-well plates in 100 μL K562 media in the presence of test compounds. Similarly, experiments with Daudi cells were initiated at 5000 cells/well and RPMI8226 cells initiated at 6000 cells/well. The cell concentrations were determined by prior dose response experiments to maximize proliferation rates. Cells were allowed to proliferate for 72 hours. During the last 2 hours, cells were labeled with 10 μL of CellQuantiBlue reagent and scanned with a Victor plate reader.

Quantification of Cellular Uptake

Compounds were exposed to PBS, K562 cells in PBS, or 50% pooled human plasma in PBS. K562 cells were used at a concentration of 1 million per mL. The fluorescence was detected using a Victor X5 plate reader with excitation at 355 nm and emissions at 405. Compounds were mixed with each biological matrix to a final concentration of 10 μM on ice. A baseline reading was measured. Compounds were incubated for one hour at 37° C. and subsequent readings were taken every 15 minutes.

Statistics

One-way ANOVA was used to calculate statistical significance. Comparisons were done relative to the control. Columns in bar graphs represent the mean+/−standard deviation. An α level of 0.05 was used.

Results

MOCCA Compounds have Low Cytotoxicity

Figure 7:
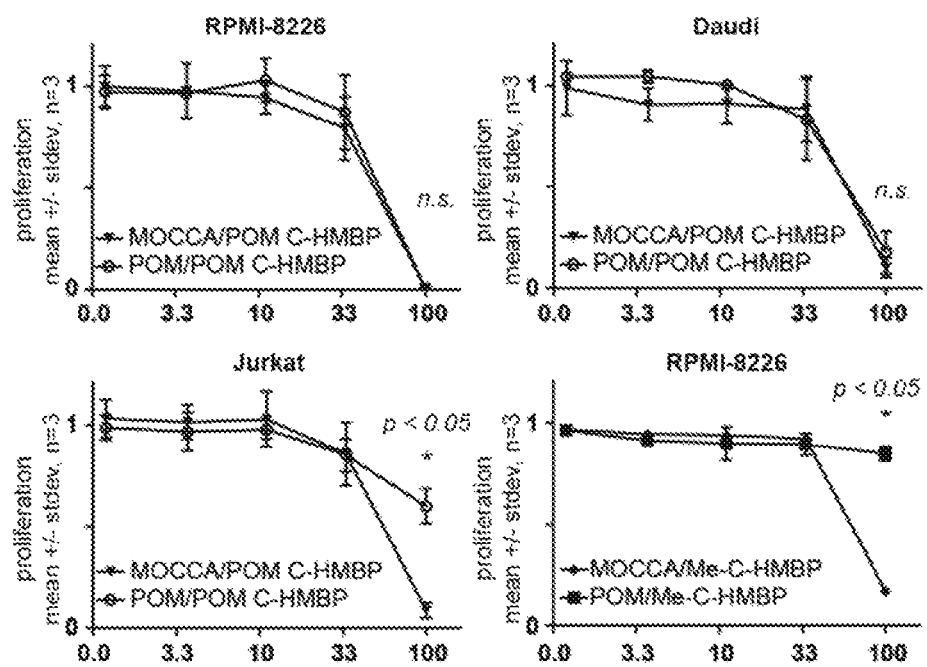
FIG. 7. The MOCCA protecting group exhibits little cellular toxicity. Effects of MOCCA prodrugs versus POM analogs on cell proliferation in which measurable $IC_{50}$ values were obtained. Indicated cell lines were treated for 72 hours with the compounds at shown concentrations and evaluated by QB assay. Statistical significance was evaluated using a paired t-test at 100 µM concentrations.

The ideal prodrug protecting group would exhibit low cellular toxicity. To establish the effects of the novel MOCCA protecting group on cell viability, the MOCCA compounds were evaluated for their ability to inhibit proliferation of several established cell lines. Notably, the MOCCA compound alone (1) exhibited no cellular toxicity in K562, Daudi, RPMI-8226, or Jurkat cells when they were exposed for 72 hours at concentrations up to 100 μM (Table 1). Additionally, treatment of K562 cells with either of the two MOCCA prodrugs also displayed no cellular toxicity when they were exposed for 72 hours at concentrations up to 100 μM. In RPMI-8226 and Daudi cells, weak but measurable $IC_{50}$ values were observed for both the POM and MOCCA versions of C-HMBP that did not differ significantly between cell lines (Table 1, FIG. 7). However, differences were observed between the POM and MOCCA versions of C-HMBP in Jurkat cells and the POM and MOCCA versions of Me-C-HMBP in RPMI-8226 cells at concentrations of 100 uM. In all cases, the toxicity was generally weak and toxic concentrations were much higher than the $EC_{50}$ values for stimulation of Vγ9Vδ2 T cells.

TABLE 1

72 hour $IC_{50}$ values in selected cell lines.

| Compound | K562 | RPMI-8226 | Daudi | Jurkat |
| --- | --- | --- | --- | --- |
| MOCCA (1) | >100 μM | >100 μM | >100 μM | >100 μM |
| C-HMBP | >100 μM | >100 μM | >100 μM | >100 μM |
| POM₂-C-HMBP (7) | >100 μM | 44 μM | 58 μM | >100 μM |
| MOCCA-POM (9) | >100 μM | 43 μM | 56 μM | 53 μM |
| Me—C-HMBP (4) | >100 μM | >100 μM | >100 μM | >100 μM |
| POM-Me—C-HMBP | >100 μM | >100 μM | >100 μM | >100 μM |
| MOCCA-Me—C-HMBP (5) | >100 μM | 64 μM | >100 μM | >100 μM |

MOCCA Compounds have Potent Cell Activity

Figure 2:
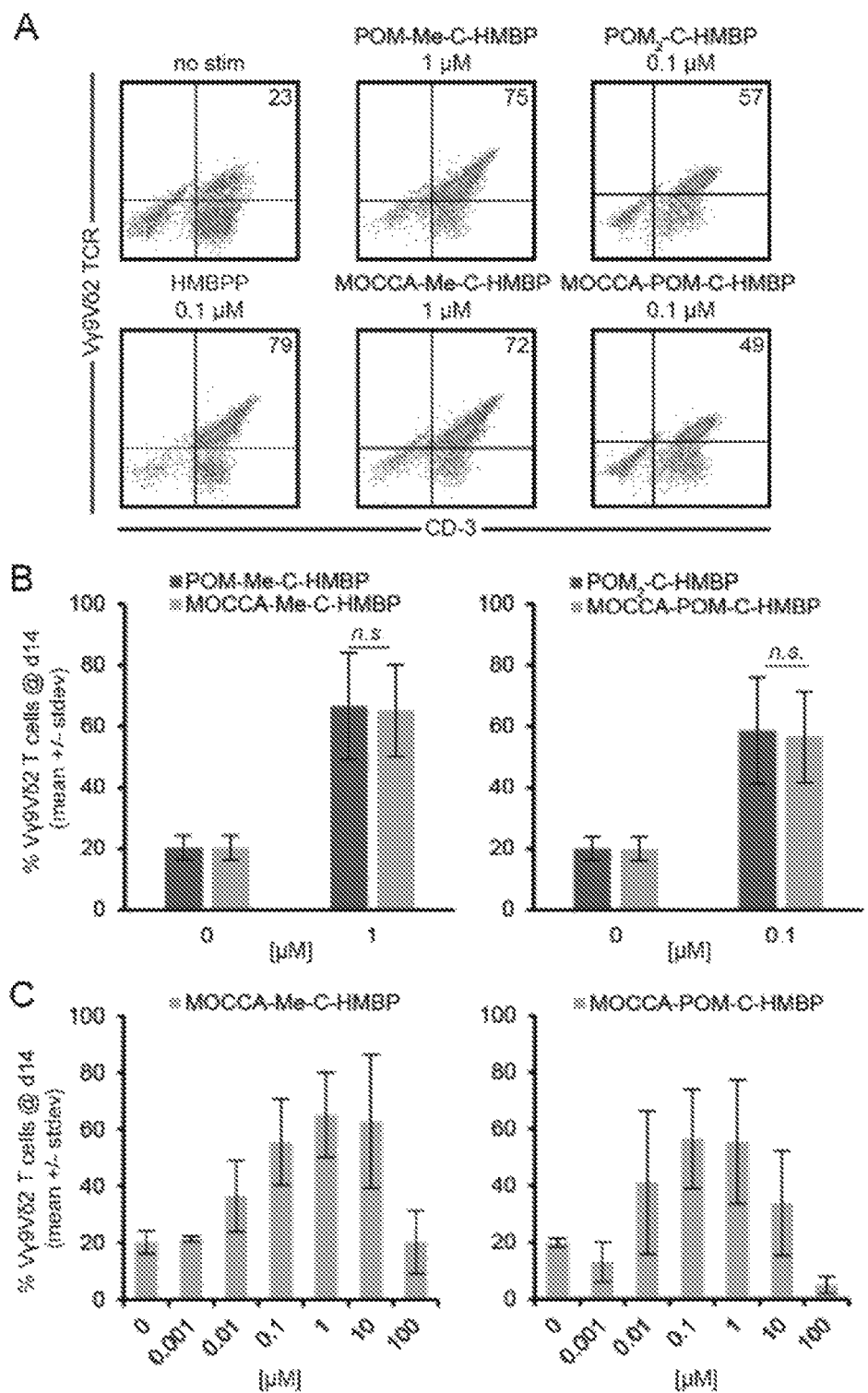
FIG. 2. MOCCA-Me-C-HMBP is a potent gamma delta T cell agonist. A) PBMCs were stimulated with MOCCA-Me-C-HMBP and phenotyping was performed to quantify the percentages of cells expressing both the gamma delta TCR and the pan T cell marker CD3. HMBPP was used as a positive control. MOCCA-Me-C-HMBP and POM-Me-C-HMBP were evaluated at a concentration (1 µM) previously shown to be maximal for POM-Me-C-HMBP. Data is representative from 3 independent experiments. B) Quantification of gamma delta T cell proliferation in response to MOCCA-Me-C-HMBP and POM-Me-C-HMBP, n=3. C) Dose response curves for MOCCA-Me-C-HMBP versus Me-C-HMBP.

The MOCCA prodrugs were also evaluated in a functional assay of their ability to stimulate proliferation of primary human gamma delta T cells. Dose response experiments were performed with the experimental compounds—MOCCA-Me-C-HMBP and MOCCA-POM-C-HMBP. POM-Me-C-HMBP, POM₂-C-HMBP, Me-C-HMBP, C-HMBP or HMBPP were used as positive controls. Unstimulated cells were used as a negative control. Cells were treated for 72 hours with test compounds, washed, then expanded for 11 additional days prior to quantification to assess proliferation. Both MOCCA-Me-C-HMBP and MOCCA-POM-C-HMBP functioned as a gamma delta T cell agonist, causing a large expansion of the population of cells that express both CD3 and the Vγ9Vδ2 T cell receptor as assessed by surface staining (FIG. 2A). This finding demonstrates that the MOCCA protecting group can effectively deliver a phosphonate payload, resulting in biological activity.

The agonist activity of POM-Me-C-HMBP was not statistically different from that of POM-Me-C-HMBP (FIG. 3B). Dose response curves (FIG. 3C) allowed us to determine that the MOCCA-Me-C-HMBP had an $EC_{50}$ of 0.018 μM while its analog Me-C-HMBP displays an $EC_{50}$ of 23 μM. Therefore the MOCCA protecting strategy offered a 1300 fold increase in activity in this assay. The activity MOCCA-Me-C-HMBP was also slightly lower than the published $EC_{50}$ value of 0.50 µM that we obtained for POM-Me-C-HMBP (Hsiao, C. H., et al., *Chem Biol*, 2014, 21, 8, 945-54). The activity of MOCCA-POM-C-HMBP was even more striking, with an $EC_{50}$ value of 0.0039 µM. This compared favorably to the published value of 0.0054 for the bis-POM analog. Taken together, this data shows minimal differences between the MOCCA and POM protecting groups of two matched pairs of compounds, suggesting that the MOCCA protecting group has similar prodrug functionality to that of the well-established and clinically-utilized POM protecting group.

TABLE 2

$EC_{50}$ values for T cell expansion

| Compound | cmpd | $EC_{50}$ | Reference |
|---|---|---|---|
| C-HMBP | | 4000 nM | Hsiao et al. |
| POM$_2$-C-HMBP | 7 | 5.4 nM | Hsiao et al. |
| MOCCA-POM-C-HMBP | 9 | 3.9 nM | none |
| Me—C-HMBP | 4 | 23000 nM | none |
| POM-Me—C-HMBP | | 520 nM | Hsiao et al. |
| MOCCA-Me—C-HMBP | 5 | 18 nM | none |

Compounds have Potent Cell Activity—K562 Lysis Assays

Figure 3:
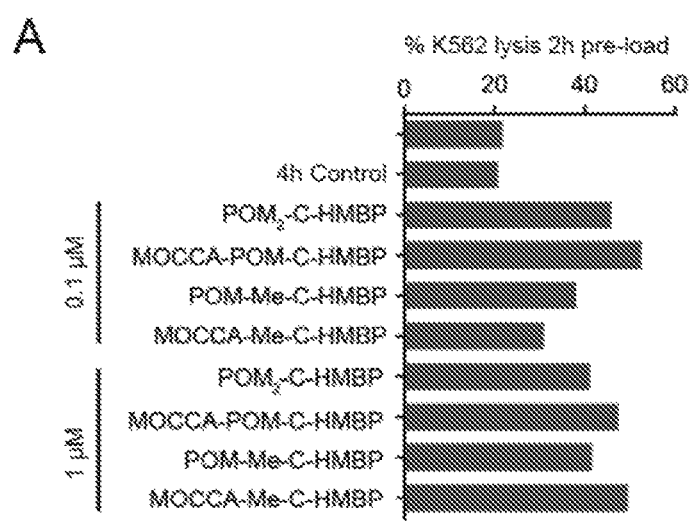
FIG. 3. MOCCA prodrugs effectively sensitize K562 cells to T cell mediated lysis.

Because the previous experiments utilized 72 hour exposure, the assays may not be sensitive enough to assess subtle differences in the rates of phosphonate release. Therefore, the activity of the novel compounds was assessed in a model of T cell mediated cytotoxicity which occurs with a shorter exposure of just 2 hour (FIG. 3).

pH Dependence and Protein Quenching of MOCCA Compounds

Figure 4:
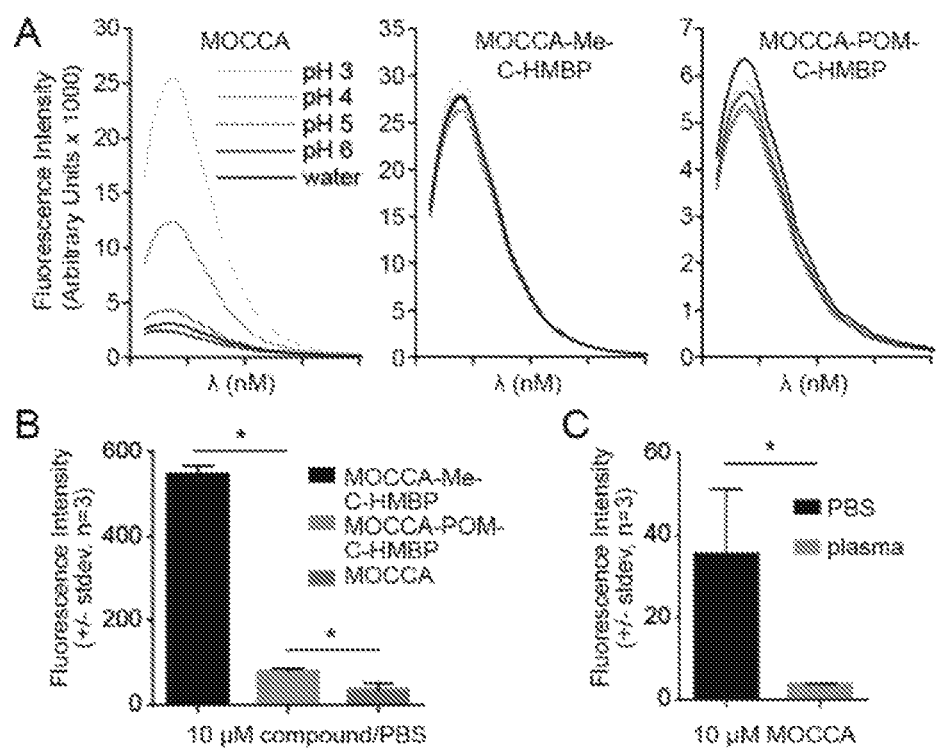
FIG. 4. pH and protein dependent changes in MOCCA fluorescence.

The use of the MOCCA prodrugs as probes with which to determine rates of biological deprotection (FIG. 4) was examined. All three compounds were readily detected by spectrophotometry with excitation maxima of 360 nm and emission maxima of 410 nm in aqueous solutions. Importantly, the fluorescence intensity of the free MOCCA group was strongly dependent upon pH of the solvent (FIG. 4A), correlating with the expected protonation of the carboxylic acid. At pH 6 the intensity of the free MOCCA group was less than 10% of its intensity at pH 3. At the same time, the fluorescence intensity of the MOCCA prodrugs was not pH dependent. Taken together, the MOCCA prodrugs would be expected to rapidly lose fluorescence intensity during metabolism at neutral pH, as the free MOCCA group is released from the prodrug and remains in the deprotonated form.

This assay was then adapted to a 384-well-plate format for use in a plate reader equipped with a 355/40 nm excitation filter and a 405/10 nm emission filter. As expected, the fluorescence intensity of MOCCA-Me-C-HMBP in PBS was much higher than that of the free MOCCA group in PBS (FIG. 4B). Additionally, the fluorescence of the free MOCCA group was further reduced when incubated in human plasma (FIG. 4C). The loss of fluorescence in plasma was likely due to quenching of the MOCCA group, as analysis by thin layer chromatography of plasma extracts confirmed that the MOCCA group had not been destroyed and further spectral analysis did not identify a shift in the excitation or emission spectra. Therefore, the esterase-mediated hydrolysis of MOCCA-Me-C-HMBP could be readily assessed by quantification of the two-step (release followed by quenching) loss of fluorescence following exposure to various biological matrices.

Kinetics of MOCCA-Me-C-HMBP Plasma Metabolism

Figure 5:
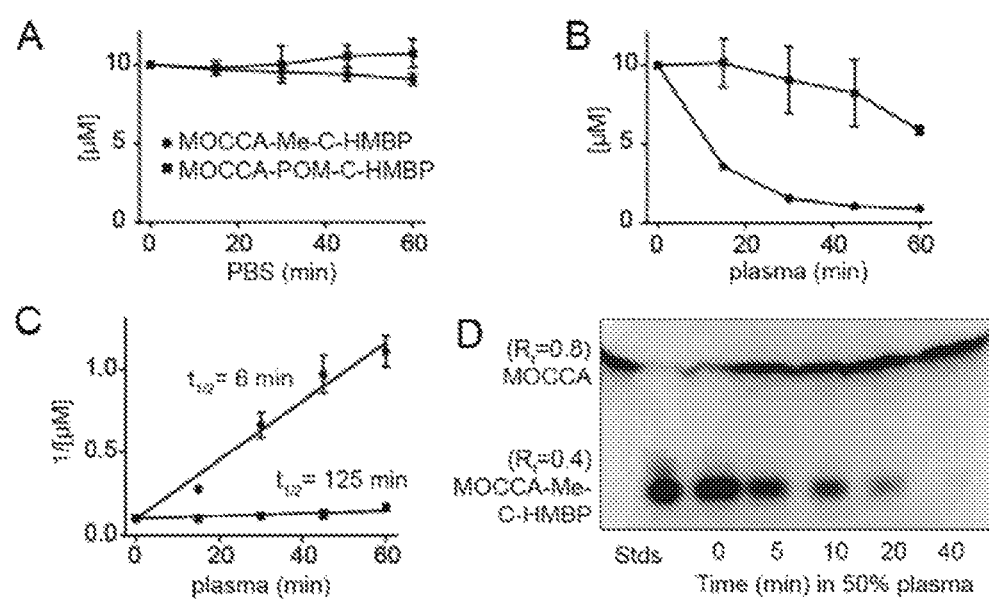
FIG. 5. MOCCA prodrugs are esterase cleavable. Kinetics of stability in A) PBS or B) 50% human plasma in PBS. C) Rate of decay fits a second order kinetics. D) Thin layer chromatography of MOCCA-Me-C-HMBP. The compound was exposed to 50% human plasma for the indicated times and resolved by TLC. Metabolism was assessed by disappearance of the compound and appearance of the MOCCA metabolite.

The prodrugs and the MOCCA protecting group were stable in PBS (FIG. 5A). However, in the presence of plasma MOCCA-Me-C-HMBP decreased with time (FIG. 5B), with $2^{nd}$ order kinetics (FIG. 5C) as assessed by spectrophotometry. The half-life was determined to be 7 minutes in this assay. Notably, MOCCA-Me-C-HMBP was metabolized more rapidly relative to the bulkier MOCCA-POM-C-HMBP. In order to confirm that the loss of fluorescence of MOCCA-Me-C-HMBP was indeed due to hydrolysis of the MOCCA-phosphonate ester, the end products were extracted and analyzed by thin layer chromatography. MOCCA-Me-C-HMBP was fully hydrolyzed to yield the free MOCCA group in the presence of human plasma within 40 minutes (FIG. 5D). Loss of the prodrug occurred at the same time as the appearance of the MOCCA free acid. The enzymatic release occurred with a half-life of 7.8 minutes in this assay. This indicates that the presence of a bicyclic aromatic group does not prevent enzymatic hydrolysis of the phosphonate ester nor does it permit rapid non-enzymatic degradation.

Kinetics of MOCCA-Me-C-HMBP Cellular Uptake

Figure 6:
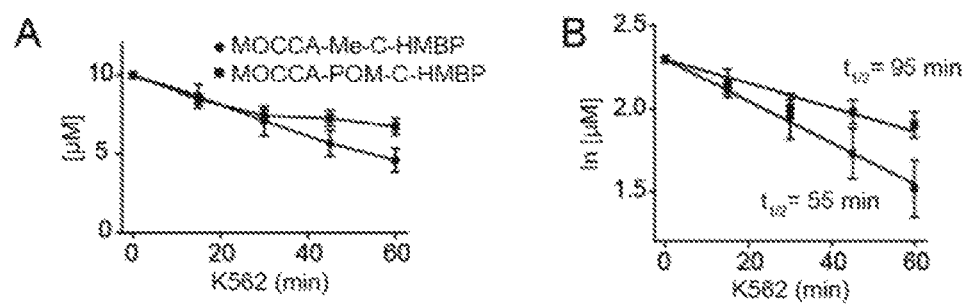
FIG. 6. MOCCA prodrugs rapidly enter cells.

The compounds were then used to examine rates of internalization into K562 cells. Surprisingly, K562 cells could rapidly decrease the extracellular concentration of the MOCCA prodrugs. The cellular metabolism of MOCCA-Me-C-HMBP was faster than that of MOCCA-POM-C-HMBP, though the difference was not as strong as was observed in plasma (FIGS. 6A and 6B). These findings demonstrate the striking efficacy of phosphonate ester prodrugs. That is, within hours, effectively all of the drug can pass through the cells.

Discussion

The utility of using a fluorescent protecting group to enhance cell penetration of a phosphonic acid has been demonstrated. The rate of hydrolysis in plasma is similar to some bis-POM compounds (Farquhar, D., et al., *Journal of Medicinal Chemistry*, 1994, 37, 23, 3902-3909).

The fluorescence approach of the instant invention is faster and requires smaller volumes of cells relative to radiolabelling approaches (Robbins, B. L., et al., *Antimicrobial Agents and Chemotherapy*, 1998, 42, 3, 612-617), or HPLC approaches (Eisenberg, E. J., *Nucleosides Nucleotides & Nucleic Acids*, 2001, 20, 4-7, 1091-1098).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A conjugate:

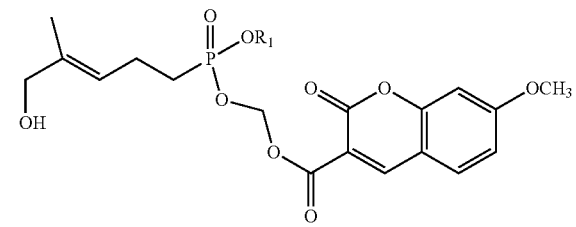

wherein $R^1$ is H, $(C_1-C_6)$alkyl, a prodrug moiety, or a protecting group, or a salt thereof.

2. A pharmaceutical composition comprising the conjugate as described in claim 1, or a pharmaceutically acceptable salt thereof, and a pharmaceutically acceptable carrier.

* * * * *